United States Patent [19]

Bonaldo

[11] Patent Number: 5,108,376
[45] Date of Patent: Apr. 28, 1992

[54] RETRACTABLE INTRAVENOUS NEEDLE ASSEMBLY

[75] Inventor: Jean M. Bonaldo, Upland, Calif.

[73] Assignee: Safetyject, Rancho Cucamonga, Calif.

[21] Appl. No.: 612,789

[22] Filed: Nov. 14, 1990

[51] Int. Cl.⁵ ............................................... A61M 5/00
[52] U.S. Cl. ................................... 604/171; 604/177; 604/198; 604/110
[58] Field of Search ............... 604/164, 165, 166, 162, 604/192, 194, 195, 197, 198, 263, 272–274, 110, 171, 174, 177; 128/919; 606/164

[56] References Cited

U.S. PATENT DOCUMENTS

| | | | |
|---|---|---|---|
| 4,388,074 | 6/1983 | Seberg et al. | 604/165 |
| 4,676,783 | 6/1987 | Jagger et al. | 604/171 |
| 4,834,708 | 5/1989 | Pillari | 604/165 |
| 4,840,613 | 6/1989 | Balbierz | 604/51 |
| 4,927,415 | 5/1990 | Brodsky | 604/164 |
| 4,935,012 | 6/1990 | Magre et al. | 604/192 |
| 4,941,874 | 7/1990 | Sandow et al. | 604/60 |
| 4,941,881 | 7/1990 | Masters et al. | 604/162 |
| 4,944,728 | 7/1990 | Carrell et al. | 604/164 |
| 4,955,863 | 9/1990 | Walker et al. | 604/165 |
| 4,964,854 | 10/1990 | Luther | 604/166 |
| 4,966,587 | 10/1990 | Baumgart | 604/164 |
| 4,969,876 | 11/1990 | Patterson | 604/171 |
| 5,013,304 | 5/1991 | Russell et al. | 604/167 |
| 5,019,049 | 5/1991 | Haining | 604/165 |

Primary Examiner—C. Fred Rosenbaum
Assistant Examiner—Mark O. Polutta
Attorney, Agent, or Firm—Robert R. Thornton

[57] ABSTRACT

A retractable intravenous needle assembly wherein a cannula is mounted on a hub within an interior passage formed in a housing in which the cannula and hub are slidably mounted so as to have the cannula point manually extend beyond the housing. Flexible wings extending laterally from the housing are manually folded upwardly to release a locking stop formed in the interior passage from engaging a locking lug on the hub. The cannula point is then manually retracted into the housing until the locking lug engages a locking recess formed in the interior passage to lock the hub in the housing. The locking recess is so located in the passage that the housing completely encloses the cannula point when the locking lug is locked in the locking recess, thus facilitating handling and disposal of the used assembly without endangering hospital personnel.

18 Claims, 2 Drawing Sheets

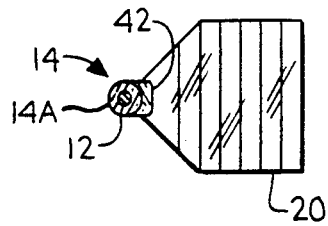
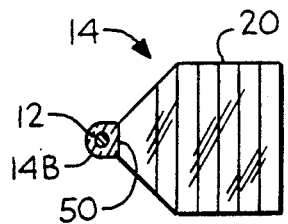
FIG. 6                    FIG. 7
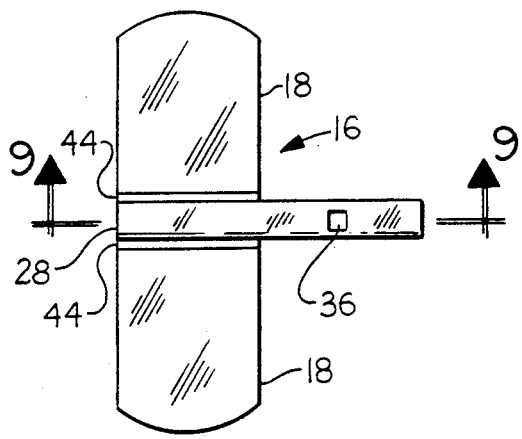
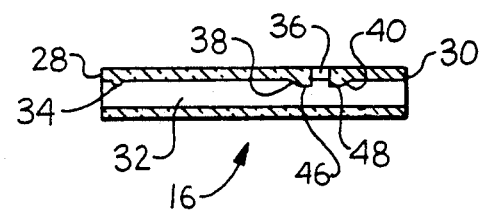
FIG. 8                    FIG. 9
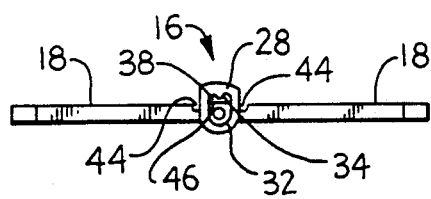
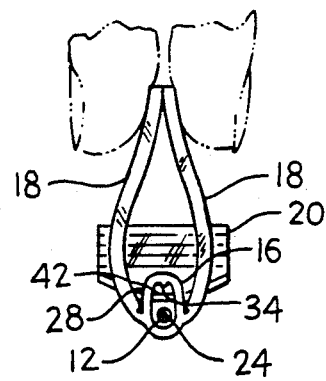
FIG. 10                   FIG. 11
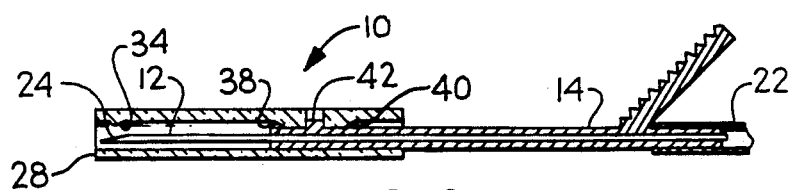
FIG. 12

RETRACTABLE INTRAVENOUS NEEDLE ASSEMBLY

BACKGROUND OF THE INVENTION

The present invention relates to an intravenous needle assembly in which the needle is retractable into the assembly.

Intravenous needle assemblies have long been utilized in the medical practice and are designed for insertion into blood vessels and similar passageways or cavities in the body, to permit infusing or withdrawing fluids. An intravenous needle of this type is described, in one particular specialized embodiment thereof, in U.S. Pat. No. 3,064,648, issued Nov. 20, 1962 to A. F. Bujan. In this device, a pair of flexible wings are utilized to fix the intravenous needle to the scalp of a patient. The needle is fixed to the flexible wings, and covered by a sheath prior to use. After utilization, the needle point is exposed and so presents a hazard during subsequent handling and disposal.

U.S. Pat. No. 4,935,011, issued Jun. 19, 1990 to J. Martin Hogan describes a sheath which may be utilized in conjunction with an intravenous needle to enclose the needle after usage so as to protect persons subsequently handling the needle against accidental sticks. The needle has a winged or butterfly housing and a sharpened cannula fixed to the housing so as to always extend therebeyond. The protective sheath encloses the wings and the cannula after use and, consequently, is comparatively bulky, as well as being relatively complex in its utilization, requiring folding and the like in order to enclose the needle. Thus, the protective sheath of U.S. Pat. No. 4,935,011 is essentially an auxiliary appliance for use with a conventional butterfly cannula, for enclosing the cannula and the housing upon which the cannula is mounted after use to avoid accident sticks.

BRIEF DESCRIPTION OF THE INVENTION

According to the present invention, a retractable intravenous needle assembly has a pointed cannula mounted on a hub which is slidably disposed within a non-circular cross-section passageway extending through a winged housing so that the cannula point extends beyond the housing and is locked against retraction thereinto by a locking lug formed on the hub engaging a depending stop boss formed in the central passageway at one end thereof. After use, the wings of the housing are folded together so as to deform the passageway cross-section at the stop boss to permit the locking lug to clear the stop, whereby the cannula may be retracted manually into the central passageway, where the locking lug engages a locking recess formed in the housing passageway so as to lock the cannula point within the passageway, thus avoiding accidental sticks during disposal of the used intravenous needle assembly.

BRIEF DESCRIPTION OF THE DRAWING

The invention may be more readily understood by referring to the accompanying drawing, in which:

FIG. 6 is a front elevation, in section, taken along lines 6—6 of FIG. 4;

FIG. 7 is a front elevation, in section, taken along lines 7—7 of FIG. 4;

FIG. 8 is a plan view of a housing for use in the present invention in conjunction with the retractable intravenous needle hub of FIG. 4;

FIG. 9 is a right side elevation, in section, taken along lines 9—9 of FIG. 8;

FIG. 10 is a front elevational view of the housing of FIG. 8;

FIG. 11 is a front elevational view of the housing of FIG. 8 in its disposition which facilitates needle retraction;

FIG. 12 is a view similar to FIG. 3, of the retractable intravenous needle assembly of the present invention in its retracted disposition.

DETAILED DESCRIPTION OF THE PREFERRED EMBODIMENT

Figure 1:
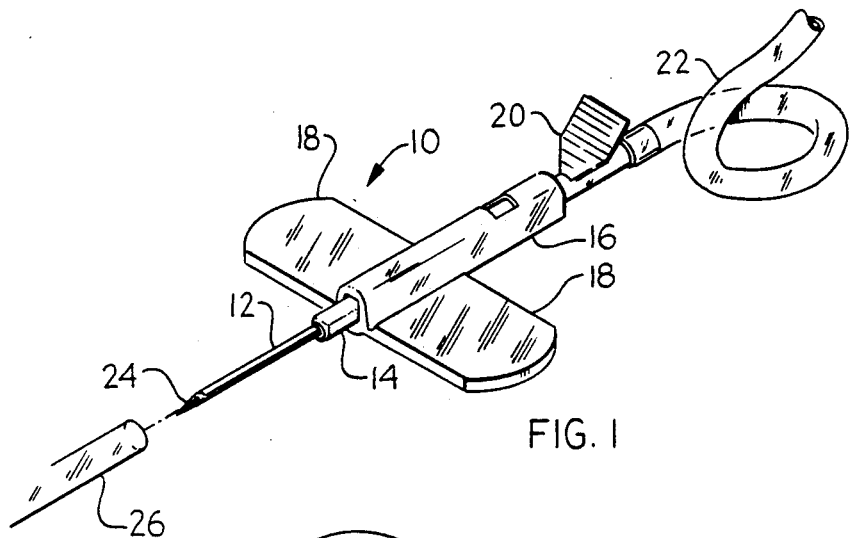
FIG. 1 is an isometric view of a retractable intravenous needle assembly according to the current invention.

Referring now to FIG. 1, there is shown an isometric view of a retractable intravenous needle assembly 10 according to the present invention. The needle assembly 10 has a cannula 12 extending outwardly from a hub 14 mounted in a housing 16. Extending laterally from the housing 16 are a pair of wings 18. At the rear of the housing 16 there is an inclined ramp 20 extending upwardly and outwardly from the hub 14 for use in retracting the cannula 12 into the housing 14, as will be explained hereinafter. The cannula 12 has a sharpened point 24. To the rear of the ramp 20, flexible tubing 22 encloses the hub 14 and thus the opposite open end 25 of the cannula 12.

Figure 2:
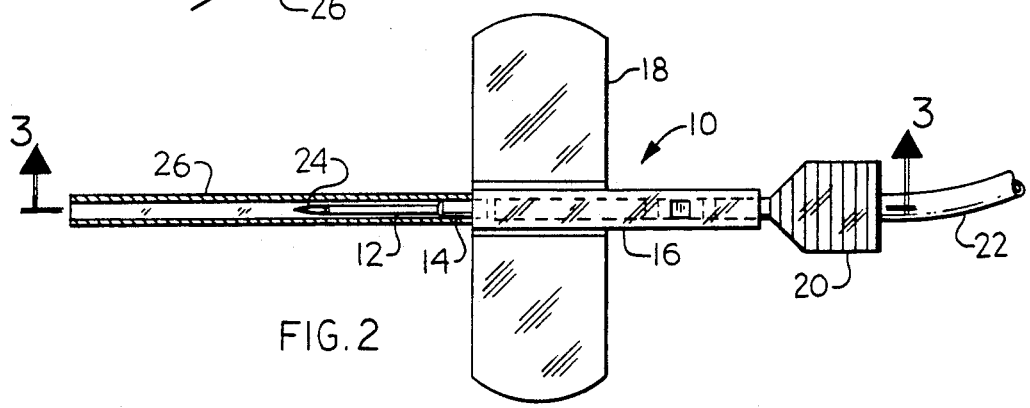
FIG. 2 is a plan view of the retractable intravenous needle assembly of FIG. 1.

Referring now to FIG. 2, the needle assembly 10 is shown with a protective sheath 26 enclosing the sharpened point 24 of the cannula 12 to protect the sharpened point prior to usage. The sheath 26 is of conventional construction and is removed at the time the cannula is to be inserted into the patient's vein.

Figure 3:
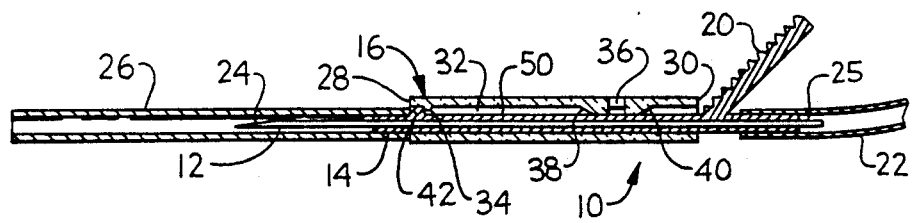
FIG. 3 is a right side elevational view, in section, taken along lines 3—3 of FIG. 2.

FIG. 3 is a right side elevation, in section, taken along lines 3—3 of FIG. 2 and illustrating the internal construction of the retractable intravenous needle assembly 10. As is shown in FIG. 3, the cannula 12 is a single ended cannula, that is, the sharpened point 24 is located at one end thereof, and at its opposite end 25, the cannula 12 terminates in a hollow blunt end suitable for permitting fluid to pass therethrough either into the cannula 12 or from the cannula 12 into the tubing 22. The hub 14 is seen to be elongated so as to extend out each of a first end 28 and a second end 30 of the housing.

The housing 16 has a longitudinal central passageway 32 extending therethrough, within which, adjacent the first end 28, a stop in the form of a depending boss 34 is formed. Adjacent to housing second end, within the passageway 32, a locking recess 36 bounded on each side by one of a pair of oppositely disposed, longitudinally aligned, spaced apart ramps 38, 40, the function of which will be described hereinafter. A locking lug 42 is formed on the hub 14 at the end thereof which is adjacent the sharpened point 24. As shown in FIG. 3, the locking lug 42 abuts and is thereby stopped by the boss 34 from entering further into the central passageway 32. Similarly, the retraction ramp 20 will be stopped by the second end 30 of the housing 16 to prevent the hub 14 from passing substantially further through the first end 28 of the housing 16 than is shown in FIG. 3. The flexible tubing 22 is connected to the hub 14 so as to enclose the open end 25 of the cannula 12 prior to use in order to permit the transfer of fluid to or from the intravenous needle assembly 10, as appropriate.

Figure 4:
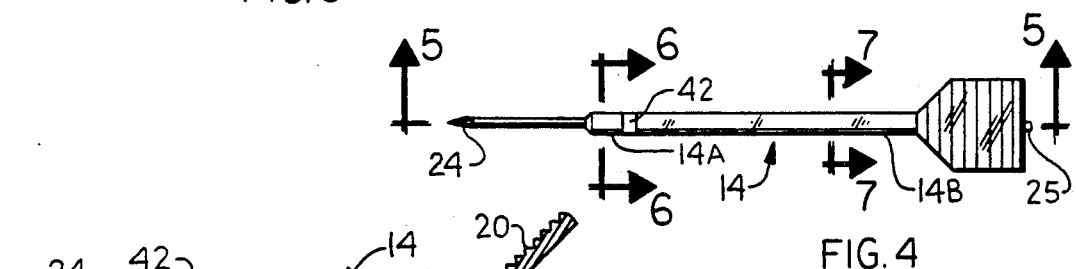
FIG. 4 is a plan view of an intravenous needle assembly hub for use in the present invention.
Figure 5:
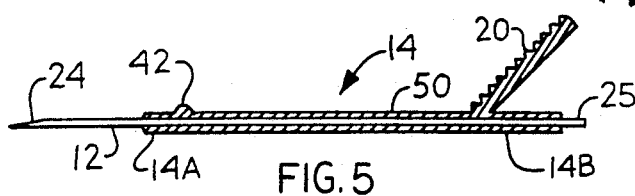
FIG. 5 is a right side elevation, in section, taken along lines 5—5 of FIG. 4.

The configuration of the hub 14 is best shown in FIGS. 4 through 7, in which FIG. 4 is a plan view of the hub 14. FIG. 5 is a right side elevation, in section, taken along lines 5—5 of FIG. 4, and FIGS. 6 and 7 are front elevational views taken along section lines 6—6 and 7—7, respectively, of FIG. 4. The hub 14 has a circular cross-sectional portion 14A which is located between the locking lug 42 and the hub end adjacent thereto and a parti-circular cross-sectional portion 14B which is located between the locking lug 42 and the ramp 20. The circular cross-section portion 14A is best seen in FIG. 6, and the parti-circular cross-sectional portion 14B is best seen in FIG. 7.

The housing 16 is shown in FIGS. 8, 9 and 10, FIG. 9 being a right side elevational view, in section, taken along line 9—9 of FIG. 8, which is a plan view of the housing 16. In FIG. 9, the ramps 38 and insertion ramp 40 are seen to be separated by the locking recess 36. As will be apparent from the description hereinafter, the locking recess 36, as shown in FIGS. 8 and 9, extends through the body of the housing 16 so as to constitute an aperture. However, it is not necessary that the locking recess 36 extend through the body so as to constitute an aperture, so long as the recess 36 is of sufficient depth with respect to the ramps 38, 40 so as to lock the locking lug 42 therebetween, as is shown in FIG. 12.

As is best seen in FIG. 10, a pair of longitudinal grooves 44 are formed in the wings 18 at their juncture with the housing 16. The grooves 44 facilitate the upward bending of the wings 18 as is illustrated in FIG. 11. Also seen in FIG. 10, which is a front elevational view of the housing 16, is the stop 34, in the form of a boss, which serves to normally stop the locking lug 42 against entering into the central passageway 32 so as to hold the cannula 12 in the extended position shown in FIG. 1. The boss 34 is shown in section in FIG. 9.

In the presently preferred embodiment shown in FIG. 10, the central passageway 32 is parti-circular in cross-section, and is complementary in cross-section to the parti-circular cross-sectional portion 14B of the hub 14, illustrated in FIG. 7. By using the complementary parti-circular cross-sections for the hub portion 14B and the housing passageway 32, rotation of the hub 14 within the central passageway 32 is inhibited. The ramps 38, 40 have flats 46, 48, respectively, which slidably engage a flat upper surface 50 formed on the parti circular hub portion 14B, see FIG. 5, so as to preclude any rotation of the hub 14 in the housing 16 in conjunction with the parti-circular cross-sectional configuration.

In order to retract the sharpened point 24 of the cannula 12 within the housing 16, the wings 18 are folded upwardly together as is shown in FIG. 11. This movement of the wings 18 causes a deformation of the cross-sectional configuration of the first end 28 of the housing 16, such that the stop 34 rises with respect to the flats 46, 48 formed on the ramps 38, 40, as is shown in FIG. 11. In this disposition of the housing 16, the locking lug 42 may pass under the stop 34 in response to urging by a finger of a user applied to the retraction ramp 20, so as to move the locking lug 42 toward the ramp 38. Once the locking lug 42 has cleared the stop 34, the wings may be unfolded, if desired, to the position shown in FIG. 10. Continued digital pressure on the retraction ramp 20 causes the locking lug 42 to engage the ramp 38, deforming the cross-sectional configuration of the housing 16 adjacent thereto so as to permit the locking lug 42 to enter the locking recess 36, as is shown in FIG. 12. In this disposition, the locking lug 42 is locked between the two ramps 38, 40 with the sharpened point 24 of the cannula 12 retracted within the housing first end 28. If not already detached, the plastic tubing 22 can then be detached from the hub 14, and the needle assembly 10 disposed of without danger of accidental sticks by the sharpened point 24 during disposal handling.

The various components of the retractable intravenous needle assembly 10 are made of conventional medical grade plastic materials, with the exception of the cannula, which is made of conventional stainless steel. For example, the cannula can be made of SS 304 grade of stainless steel, the hub made of grade PD 626 PROFAX polypropylene distributed by Himont USA, Inc. of Wilmington, Del., and the housing made of 2363 Series polyurethane elastomer distributed by Alpha Chemical & Plastics Corporation of Newark, N.J. It is to be understood that these examples of materials from which the components of the retractable intravenous needle assembly of the present invention may be constructed are given by way of example, and are not to be considered as limitations upon the present invention as claimed herein.

Similarly, while the figures show the use of a parti-circular cross-sectional configuration with a flat upper surface on the hub for the complementary hub and passage configurations as the presently preferred embodiment, other configurations which inhibit or prevent hub rotation in the passage can be used. For example, cross-sectional polygonal shapes, such as triangles, rectangles, hexagons, etc. can be utilized, although such configurations may be more difficult to manufacture. Other configurations, such as a keyed slot, oval and elliptical cross-sections can also be used to prevent rotation without departing from the scope of the present invention as claimed hereinafter, except as such alternate embodiments may be expressly excluded by the limitations contained in certain of the following claims.

The invention claimed is:

1. A retractable intravenous needle assembly comprising:
a housing having a central passageway extending longitudinally therethrough, said passageway having a first end and a second end;
a stop formed in the passageway in proximity to the first end thereof;
locking means formed in said passageway remote from the first end thereof;
an elongated hub;
a cannula having a sharpened point at one end, said cannula being mounted in said hub so as to extend longitudinally therethrough so that at least the pointed end of said cannula is disposed beyond the hub, said hub having a locking lug formed thereon in proximity to said pointed end, said hub being slidably positioned in said passageway so that said stop is normally disposed between said locking lug and said locking means, and when so disposed, is normally operable to prevent said lug from passing by the stop into the passageway;

release means fixed to the exterior of said housing adjacent said stop and operable when actuated to deform the cross-sectional configuration of said passageway at said stop so as to permit the locking lug to pass by the stop when urged toward the locking means, said locking means being operable when in engagement with said locking lug to lock said hub to said housing in a disposition such that the cannula pointed end is contained within the housing passageway.

2. A retractable intravenous needle assembly according to claim 1, and including manual operating means longitudinally aligned with said hub and extending outwardly therefrom exteriorly of the housing second end for manually sliding said hub longitudinally along said passageway to move said locking lug from beyond said stop to said locking means upon actuation of said release means.

3. A retractable intravenous needle assembly as claimed in claim 1, and including means for preventing the relative rotation of the hub with respect to the housing.

4. A retractable intravenous needle assembly as claimed in claim 3, and in which said rotation preventing means is comprised by complementary non-circular configurations of at least a portion of the passageway and the hub which engage one another.

5. A retractable intravenous needle assembly as claimed in claim 4, and in which the cross-sectional configuration is parti-circular.

6. A retractable intravenous needle assembly as claimed in claim 1, and in which the locking means is comprised by a recess formed in the passageway.

7. A retractable intravenous needle assembly as claimed in claim 6, and in which the locking means recess is comprised by a pair of opposed ramps longitudinally disposed in said passageway with the recess formed therebetween.

8. A retractable intravenous needle assembly as claimed in claim 7, and including means for preventing the relative rotation of the hub with respect to the housing.

9. A retractable intravenous needle assembly as claimed in claim 8, and in which the rotation preventing means includes at least one ramp which engages a non-arcuate surface formed on the hub to prevent rotation.

10. A retractable intravenous needle assembly as claimed in claim 2, and in which said manual operating means is comprised by an inclined ramp formed on said hub so as to be normally disposed outside of the housing passageway in proximity to said second end thereof and operable in response to digital urging by a user away from said second end to move said hub so as to move said locking lug from beyond said stop to said locking means upon actuation of said release means.

11. A retractable intravenous needle assemble as claimed in any one of claims 1 through 10, and in which said release means is comprised by a pair of lateral wings oppositely disposed on said hub and operable when folded together to deform the passageway so as to permit the locking lug to pass by the stop into the passageway toward the locking means.

12. A retractable intravenous needle assembly as claimed in claim 11, and in which the stop is a boss.

13. A retractable intravenous needle assembly comprising:
a cannula having a sharpened point at one end;
an elongated hub of a first preselected cross-sectional configuration, said needle being mounted in said hub so as to extend longitudinally therethrough so that at least the pointed end is disposed beyond one end of the hub, said hub having a locking lug formed thereon in proximity to said end;
(a) a housing having a longitudinal central passageway extending therethrough, said passageway having a second preselected cross-sectional configuration generally complementary to said first preselected cross-sectional configuration over at least a portion of the passageway so as to inhibit rotation of the hub in the passageway;
(b) a stop formed in the passageway so as to extend thereinto in proximity to one end thereof; and
(c) locking recess means formed in said passageway adjacent the other end thereof and operable when in engagement with said locking lug to lock said hub to said housing in a disposition such that the cannula point is contained within the housing passageway,
said hub being normally positioned in said passageway so that said stop is disposed between said locking lug and said locking recess means and adjacent said locking lug; and
release means fixed to the exterior of said housing adjacent said stop and operable in response to digital manipulation to deform the cross-sectional configuration of said passageway at said stop so as to permit the locking lug to pass by the stop when urged by movement of the hub toward the locking recess means.

14. A retractable intravenous needle assembly according to claim 13, and including manual operating means longitudinally aligned with said hub and extending outwardly therefrom exteriorly of the housing other end for manually sliding said hub longitudinally along said passageway to move said locking lug from beyond said stop to said locking means.

15. A retractable intravenous needle assembly comprising:
a housing having a longitudinal parti-cylindrical passageway extending therethrough, said passageway having a first end and a second end, said housing having a depending stop extending into said passageway adjacent said first end;
a longitudinal hub of a complementary parti-cylindrical cross-section along at least a portion thereof, said hub
(a) being slidably disposed in said passageway so as to normally extend out of each end thereof, and
(b) having a pointed cannula extending longitudinally therethrough so that said cannula point extends out of the housing end having the depending stop;
a locking lug formed on said hub so as to be normally positioned exteriorly of and engageable with said stop to normally prevent the cannula point from sliding into the passageway;
a pair of flexible lateral wings formed on said housing adjacent said stop and operable when folded together to deform said passageway cross-section at said stop so as to permit the locking lug and the cannula point to slide past the stop into the housing passageway; and
locking means formed in the passageway between said stop and said second end and operable to engage the locking lug so as to lock the hub to the housing with the cannula point contained within the passageway.

16. A retractable intravenous needle assembly as claimed in claim 15, and in which the locking means is comprised by a recess formed in the passageway.

17. A retractable intravenous needle assembly as claimed in claim 16, and in which the locking means recess is comprised by a pair of oppositely extending ramps disposed longitudinally in said passageway so that the recess is formed therebetween.

18. A retractable intravenous needle assembly as claimed in any one of claims 15, 16 or 17, and including manual operating means longitudinally aligned with said hub and extending outwardly therefrom exteriorly of the housing other end for manually sliding said hub longitudinally along said passageway to move said locking lug from beyond said stop to said locking means.

* * * * *